US009351088B2

(12) United States Patent
Rini et al.

(10) Patent No.: US 9,351,088 B2
(45) Date of Patent: May 24, 2016

(54) EVALUATION OF SOUND QUALITY AND SPEECH INTELLIGIBILITY FROM NEUROGRAMS (71) Applicants: MED-EL Elektromedizinische Geraete GmbH, Innsbruck (AT); Technische Universität München, München (DE)

(72) Inventors: Stefano Rini, San Fermo (IT); Michael Drews, Olching (DE); Michele Nicoletti, München (DE); Werner Hemmert, Garching (DE)

(73) Assignees: MED-EL Elektromedizinische Geraete GmbH, Innsbruck (AT); Technische Universität München, München (DE)

( * ) Notice: Subject to any disclaimer, the term of this patent is extended or adjusted under 35 U.S.C. 154(b) by 102 days.

(21) Appl. No.: 14/305,094

(22) Filed: Jun. 16, 2014

(65) Prior Publication Data
US 2014/0294188 A1    Oct. 2, 2014

Related U.S. Application Data (63) Continuation of application No. PCT/US2014/018879, filed on Feb. 27, 2014.

(60) Provisional application No. 61/770,537, filed on Feb. 28, 2013.

(51) Int. Cl.
*H04R 29/00* (2006.01)
*H04R 25/00* (2006.01)
(Continued)

(52) U.S. Cl.
CPC ............ *H04R 25/70* (2013.01); *A61B 5/048* (2013.01); *A61B 5/04845* (2013.01);
(Continued)

(58) Field of Classification Search
CPC . A61B 5/125; A61B 5/04845; A61N 1/36032
USPC ................................................ 381/60; 607/57
See application file for complete search history.

(56) References Cited

U.S. PATENT DOCUMENTS 5,991,663 A *  11/1999  Irlicht et al. ................ 607/57
2006/0140418 A1 *  6/2006  Koh et al. ................. 381/98
(Continued)

FOREIGN PATENT DOCUMENTS

WO    WO 2012/082721    6/2012    ............. A61B 5/12
WO    WO 2013/009805    1/2013    ............. H04R 25/00

OTHER PUBLICATIONS

Cole et al., *The ISOLET spoken letter database*, Tech. Rep. CSE 90-004, Oregon Graduate Institute of Science and Technology, 1990.
(Continued)

*Primary Examiner* — Ahmad F Matar
*Assistant Examiner* — Katherine Faley
(74) *Attorney, Agent, or Firm* — Sunstein Kann Murphy & Timbers LLP (57) ABSTRACT An approach is described for evaluating a selected hearing stimulation strategy in a hearing impaired patient. A healthy neurogram represents a normal auditory neural response to a selected sound input by a healthy auditory system. An impaired neurogram represents an impaired auditory neural response to the selected sound input by a hearing impaired patient auditory system using the hearing stimulation strategy. The impaired neurogram is compared to the healthy neurogram based on: i. partitioning the neurograms into corresponding temporal and frequency domain tiles, ii. determining local variability between corresponding individual tiles by comparison of selected tile features, iii. determining global variability between the neurograms by weighted averaging of the individual tile comparisons, and iv. developing from the local and global variabilities a perception estimate representing effectiveness of the selected hearing stimulation strategy in approaching normal healthy hearing for the implanted patient.

16 Claims, 6 Drawing Sheets
(3 of 6 Drawing Sheet(s) Filed in Color)

(51) Int. Cl.

| | | |
|---|---|---|
| *A61N 1/36* | (2006.01) | |
| *A61B 5/048* | (2006.01) | |
| *A61B 5/0484* | (2006.01) | |
| *A61B 5/12* | (2006.01) | |
| *A61N 1/05* | (2006.01) | |
| *A61B 5/00* | (2006.01) | |

(52) U.S. Cl.
CPC ........... *A61B 5/125* (2013.01); *A61N 1/36032* (2013.01); *H04R 25/606* (2013.01); *A61B 5/7246* (2013.01); *A61N 1/0541* (2013.01); *H04R 2225/67* (2013.01)

(56) References Cited

U.S. PATENT DOCUMENTS

| | | | |
|---|---|---|---|
| 2007/0167691 A1* | 7/2007 | Causevic | 600/301 |
| 2009/0018615 A1 | 1/2009 | Blamey et al. | 607/57 |
| 2010/0131262 A1 | 5/2010 | Gruhn et al. | 704/8 |

OTHER PUBLICATIONS

Elhilali et al., *A Spectro-Temporal Modulation Index (STMI) for Assessment of Speech Intelligibility*, Speech Communication, vol. 41, No. 2, pp. 331-348; 2003.

Wang et al., *Image Quality Assessment: From Error Visibility to Structural Similarity*, IEEE Transactions on Image Processing, vol. 13, No. 4, pp. 600-612, 2004.

Bondy et al., *Predicting Speech Intelligibility From a Population of Neurons*, in NIPS 2003 Conference Proceedings: Advances in Neural Information Processing Systems 16, eds. S. Thrun, L. Saul and B. Schölkopf, MIT Press, Cambridge, MA, pp. 1409-1416; 2004.

Hines et al., *Speech Intelligibility prediction using a Neurogram Similarity Index Measure*, Speech Communication. vol. 54 No. 2. 2012. 306-320.

International Searching Aurthority—US, International Search Report and Written Opinion, PCT/US2014/018879; dated May 21, 2014. 12 pages.

* cited by examiner

EVALUATION OF SOUND QUALITY AND SPEECH INTELLIGIBILITY FROM NEUROGRAMS

This application is a continuation of Patent Cooperation Treaty Application PCT/US2014/018879, filed Feb. 27, 2014, which in turn claims priority from U.S. Provisional Patent Application 61/770,537, filed Feb. 28, 2013, which is incorporated herein by reference in its entirety.

TECHNICAL FIELD

The present invention relates to ear implants, and more specifically to custom fitting of ear implant systems such as cochlear implants. Applications also include the evaluation of audible differences, which is relevant for quality estimations of sound coding (i.e. of lossy data compression algorithms), sound transmission systems, and hearing aids.

BACKGROUND ART

Figure 1:
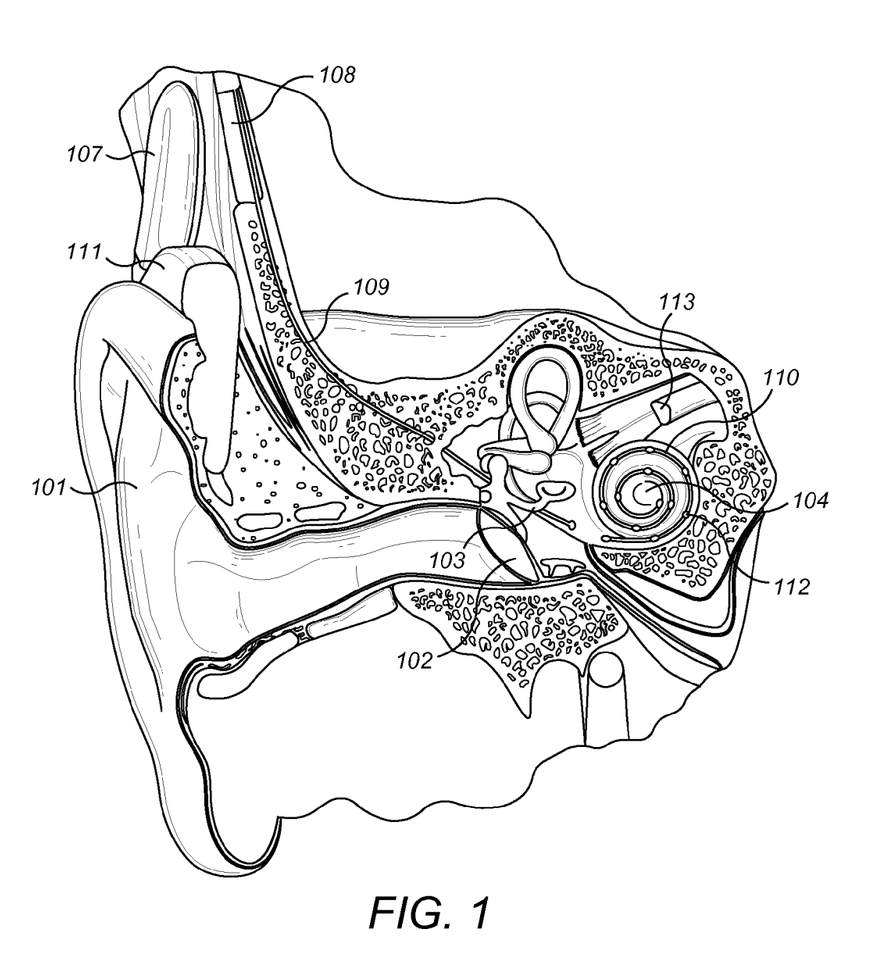
FIG. 1 shows anatomical structures in a human ear having a cochlear implant system.

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode contact can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple stimulation contacts 112 on its surface that provide selective stimulation of the cochlea 104.

Figure 2:
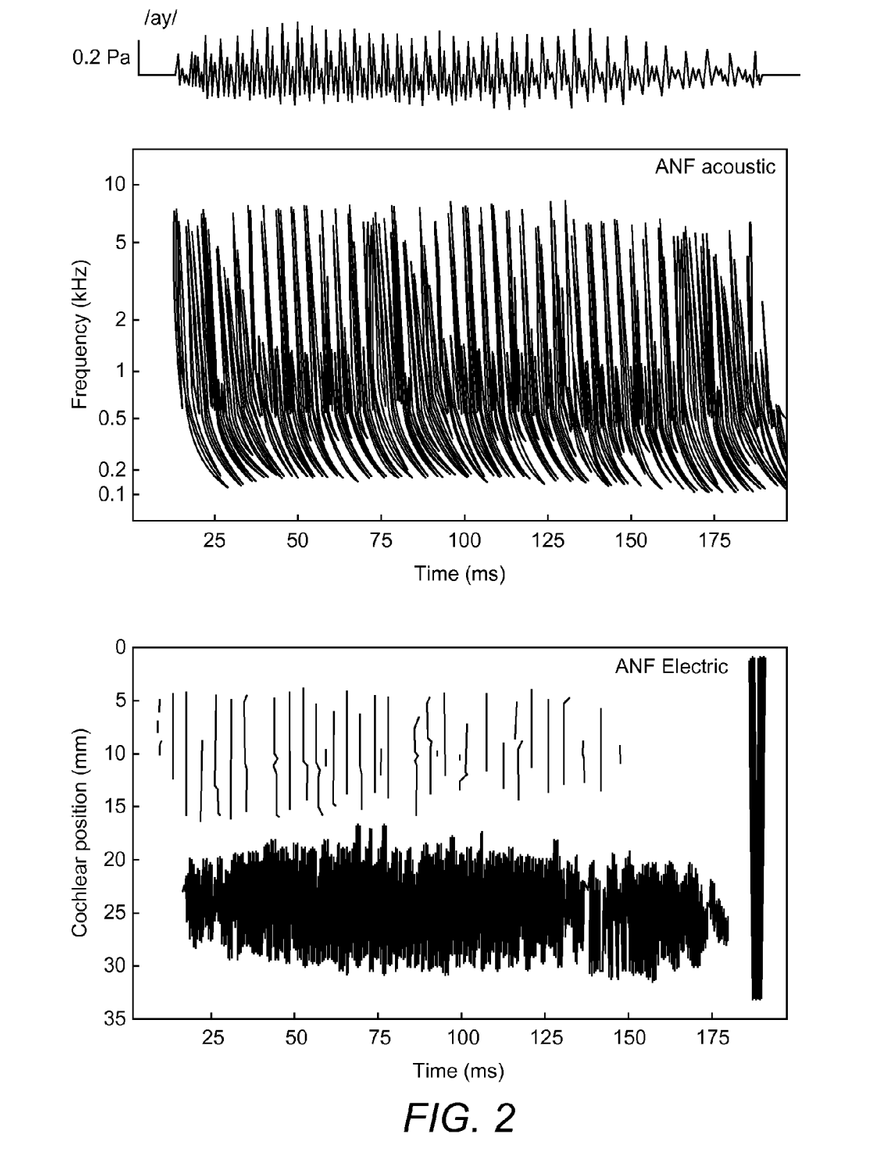
FIG. 2 shows sound pressure characteristics of a spoken "A" (/ay/) and corresponding neurogram responses.

Current cochlear implant coding strategies are mostly straight-forward sound processing schemes which map the different sound frequency channels onto different locations along the biological frequency map within the cochlea. FIG. 2 shows one example of the processing of a signal using the cochlear implant stimulation (CIS) stimulation strategy. The top of FIG. 2 shows the sound pressure characteristics of a spoken "A" (/ay/) at a sound level of 67.2 dB. The middle waveform in FIG. 2 shows a normal healthy auditory system response. The bottom waveform in FIG. 2 shows a neural response of the auditory nerve fibers under CIS stimulation.

Contemporary coding strategies were developed to code the spectral structure of sounds which provides sufficient cues for speech understanding. However, the complex time-place patterns observed in the intact ear cannot yet be replicated. This is also due to technical limitations as for example the channel crosstalk between electrode channels which imposes strong limitations on electrically evoked neuronal excitation patterns.

The evaluation of sound quality and speech intelligibility for the purposes of a hearing prosthesis is a complex task that is connected to many perceptual factors. The processing of the auditory system from the outer ear to the auditory nerve fibers can be represented in one or more neurograms such as the ones shown in FIG. 2 where the x-axis represents time and the y-axis logarithmically represents center frequency of the auditory nerve fiber. Neurograms can be used to efficiently predict the intelligibility aspects that relate to the first parts of the auditory pathway.

The literature in the field has proposed various speech evaluation tools. Back in 1947, French and Steinberg (*Factors Governing the Intelligibility of Speech Sounds*, Journal of the Acoustical Society of America, vol. 19, no. 1, pp. 90-119, incorporated herein by reference) proposed an articulation index (AI) to evaluate speech intelligibility of an audio signal purely as a function of the signal-to-noise-ratio (SNR) dependent on a specific threshold of hearing in twenty frequency bands. In each band the chosen SNR is used to model the overall sound quality, which can be adapted to specific hearing losses.

Bondy et al., *Predicting Speech Intelligibility from a Population of Neurons*, Advances in Neural Information Processing Systems, vol. 16, 2003 (incorporated herein by reference) described a Neural Articulation Index (NAI) as a variation of the AI based on a weighted sum of the SNR of the firing rates in seven frequency bands of a neurogram.

Elhilali et al., *A Spectro-Temporal Modulation Index (STMI) for Assessment of Speech Intelligibility*, Speech Communication, vol. 41, no. 2, pp. 331-348, 2003 (incorporated herein by reference) described using a Spectro-Temporal Modulation Index to evaluate the quality of an auditory model to spectro-temporal modulations under different distortions such as noise, reverberations etc. and attempted to predict speech intelligibility under the influence of these distortions using simple averaging.

Hines and Harte, *Speech Intelligibility from Image Processing*, Speech Communication, vol. 52, no. 9, pp. 736-752, 2010 (incorporated herein by reference) proposed using an image processing technique known as Structural Similarity Index Measure (SSIM, or later NSIM—neurogram similarity index measure) developed by Wang et al. *Image Quality Assessment: From Error Visibility to Structural Similarity*, IEEE Transactions on Image Processing, vol. 13, no. 4, pp. 600-612, 2004 (incorporated herein by reference) which regarded neurograms as images and assessed the similarity between them.

Current comparison methods for neurograms (or related representations of auditory perception) such as NI, NIT, STMI, SSIM and NSIM focus on predicting speech intelligibility in the presence of noise and other signal distortions. They try to estimate the overall quality in the neural representation of a given sound. The quality indexes NI, NIT, STMI are based on average properties of neurograms which are too coarse to be effective in capturing perceptual aspects. Also they do not allow for an adequate comparison between different neurograms which is important when designing stimulation strategies. The NSIM by Hines regards neurograms as images and attempts to predict intelligibility by comparing a degraded neurogram with a reference neurogram under normal hearing conditions. All these approaches do not exploit all relevant information coded in the temporal sequence of auditory neuronal spike trains and are inspired by engineering applications which do not necessarily fit the complex framework of human sound perception.

SUMMARY

Embodiments of the present invention are directed to evaluating a selected hearing stimulation strategy in a hearing impaired patient. A healthy neurogram represents a normal auditory neural response to a selected sound input by a healthy auditory system. An impaired neurogram represents an impaired auditory neural response to the selected sound input by a hearing impaired patient auditory system using the hearing stimulation strategy. The impaired neurogram is compared to the healthy neurogram based on: i. partitioning the neurograms into corresponding temporal and frequency domain tiles, ii. determining local variability between corresponding individual tiles by comparison of selected tile features, iii. determining global variability between the neurograms by weighted averaging of the individual tile comparisons, and iv. developing from the local and global variabilities a perception estimate representing effectiveness of the selected hearing stimulation strategy in approaching normal healthy hearing for the implanted patient.

The perception estimate may further be based on a computational model of a hearing prosthesis using the selected hearing stimulation strategy. An approximate evaluation of the Levenshtein distance between the selected tile features may be used for determining local variability; for example, using the two-dimensional extension of the Needleman-Wunsch algorithm applied to a matrix containing neurogram instantaneous firing rate. A weighted partition sum may be used for determining global variability. Comparing the neurograms may be based on a rate-place code with coarse temporal resolution (e.g. 10 milliseconds) and/or temporal fine structure with temporal resolution less than 1 millisecond depending on the resolution used for comparing the neurograms.

Another embodiment of this invention can be used to evaluate sound quality. In this case neurograms are compared for the original and the test sound using the same (healthy) inner ear model. In yet another embodiment neurograms from sounds processed by a hearing aid and a hearing impaired inner ear model are compared with neurograms from a healthy inner ear model to optimize hearing aid signal processing.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5 A-D shows an example of neurogram partitioning and weighting according to one embodiment of the present invention.

DETAILED DESCRIPTION

Embodiments of the present invention are directed to a new general approach to assess the overall quality of neurograms which is based on acoustic- and insights from neuroscience into the human auditory system and which considers both local and global differences among spectrograms in both the temporal and frequency domains. This can be specifically used for evaluating, predicting and improving speech intelligibility using the set of instantaneous neural spike patterns in the auditory nerve. A matching algorithm transforms a neurogram through a sequence of single-element operations to another reference neurogram. The cost associated with this sequence of transformations then defines a distance or a similarity index between neurograms which allows the solving on a perceptual basis of different tasks regarding sound quality and intelligibility estimation. Along with computational models of hearing prostheses (e.g., cochlear implants) this metric can be used to improve current stimulation designs and increase the perceived sound quality and speech intelligibility of hearing impaired patients. This approach has a greater level potential for adaptability than prior art approaches such AI and NAI and can thus more accurately model patient hearing abilities. A specific algorithm can be tuned to both local and global features of neurograms and so has great flexibility.

Figure 3:
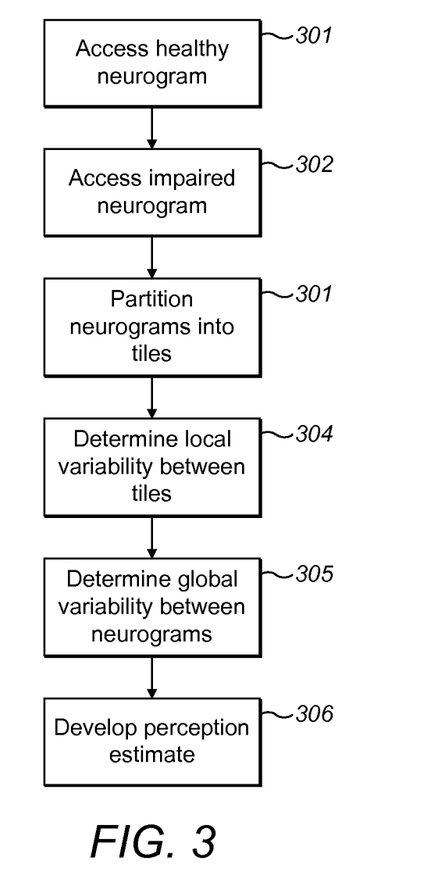
FIG. 3 shows various logical steps in a method according to one embodiment of the present invention.

FIG. 3 shows various logical steps in a method according to one embodiment of the present invention. First the algorithm accesses a healthy neurogram that represents a normal auditory neural response to a selected sound input by a healthy auditory system, step 301. An impaired neurogram also is accessed, step 302, that represents an impaired auditory neural response to the selected sound input by a hearing impaired patient auditory system using the hearing stimulation strategy. Then the neurograms are compared starting with partitioning them into corresponding temporal and frequency domain tiles, step 303. Then local variability between corresponding individual tiles is determined, step 304, by comparison of selected tile features. From that, global variability between the neurograms can be determined, step 305, by weighted averaging of the individual tile comparisons. The local and global variabilities are then used to develop a perception estimate representing effectiveness of the selected hearing stimulation strategy in approaching normal healthy hearing for the implanted patient, step 306.

One specific way to determine local similarity is by using a two dimensional extension of the Needleman-Wunsch algorithm (also known as Seller's algorithm), which is a dynamic programming technique used to evaluate the Levenshtein distance between two one-dimensional sequences (e.g. letters, DNA sequences, etc.). The Levenshtein distance is defined as the minimum cost required to change a given sequence into another using single-element operations—insertion, deletion or substitution—each having a given cost. The Levenshtein distance between two one dimensional sequences can be obtained through an optimal matching algorithm that provides the minimum number of transformations to go from one sequence to another.

The original Needleman-Wunsch algorithm was derived for one dimensional sequences. Two dimensional extensions of this algorithm have been proposed in literature and although optimality is not strictly given in the two-dimensional case these yield reasonable results for the present purposes. We will refer to this two-dimensional algorithm to approximate the Levenshtein distance as the "2DL algorithm" and apply this algorithm to a matrix which contains the instantaneous firing rate of a given neurogram's time/frequency tile. This can be realized by using a variation of the 2DL algorithm in which the substitution of an element in the two dimensional array with another element has a substitution cost that is proportional to the difference between the values (amplitude), the horizontal (time) and vertical (frequency) indices of the two elements.

Figure 4:
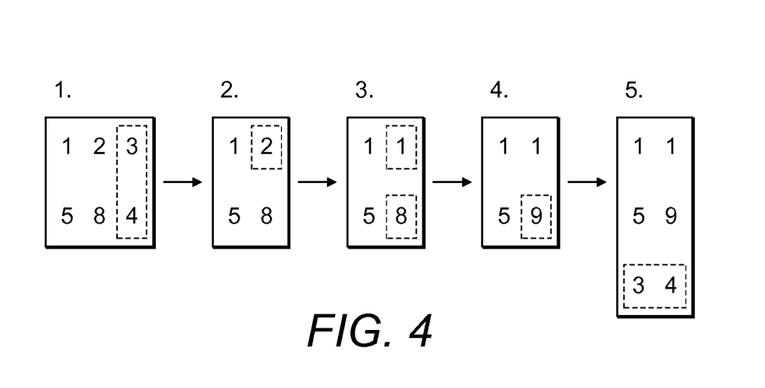
FIG. 4 shows an example of matrix transformation as performed by embodiments of the present invention.

One specific example of the 2DL is shown in FIG. 4, where elements marked with red are deleted, elements marked with blue are inserted, and elements marked with green are substituted (or "shifted"). In this example, the cost of deletion/insertion is defined as 1, the cost of changing the horizontal or vertical index of an element by 1 (and therefore shifting it) or changing its amplitude by 1 is defined as being 0.1. The overall cost then is 4.2 in this example.

To determine the global similarity, the local similarity index is applied to different portions of the spectrogram ("tiles") and the impact of each contribution is combined to obtain the overall similarity index. The simplest partition of the neurograms to be compared is a uniform tiling in both frequency in time but any particular partitioning may be feasible. The local similarity indexes from each partition tile can be combined in different ways to obtain the overall similarity indexes.

Figure 5A:
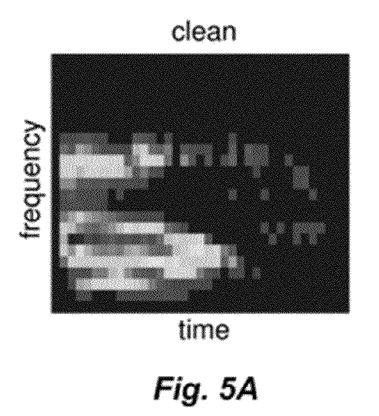
Figure 5B:
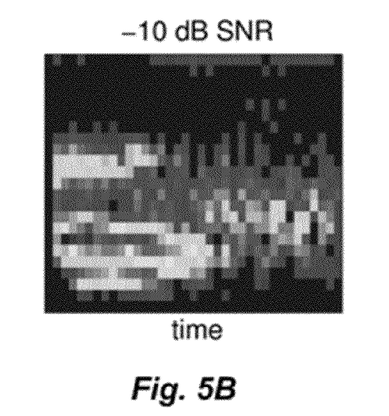
Figure 5C:
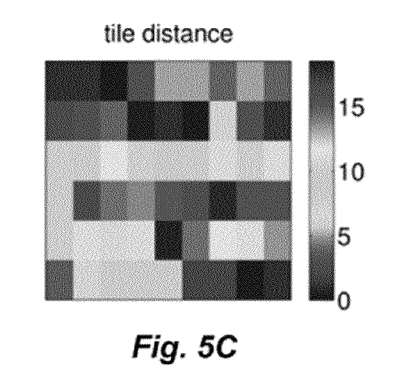
Figure 5D:
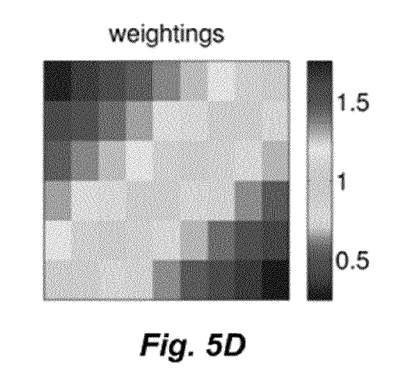

For example, a weighted sum of the partition is one possible choice for combining local similarities indexes. In FIG. 5 A-D, two downsampled neurograms—a clean spoken "A" (FIG. 5A) and a noisy one (−10 dB SNR of pink noise, FIG. 5B)—are partitioned into 6×9 local tiles (each tile containing 4 frequency channels and 0.1 sec in time) and the similarity indices between them are calculated by means of local tile distances as shown in FIG. 5C where red (light gray) represents larger distances and blue (darker gray) represents smaller distances. A weighting matrix as shown in FIG. 5D—increasing in frequency and decreasing in time—is then assigned to each tile. The distance between the two neurograms then decreases as lower cost is associated to lower frequencies where pink noise has the most significant impact. The single-operation costs can be seen as local parameters which can be adjusted in each tile to account for different perceptual relevance in different time/frequency slots of the neurogram.

Speech intelligibility can be evaluated using the proposed similarity index to perform a classification task of different vowels under pink noise of varying intensities. In one set of experiments was performed using uniform tiling, uniform cost in each tile, and equal weighting of the local costs. Neurograms were produced for 5 different vowels of 2 different speakers of the ISOLET database (R. Cole, Y. Muthusamy and M. Fatny, "The isolet spoken letter database", Tech. Rep. CSE 90-004, Oregon Graduate Institute of Science and Technology, 1990; incorporated herein by reference) in clean conditions and with SNRs from −14 dB SNR to −1 dB SNR. A neurogram was classified as belonging to a certain vowel when the distance from the corresponding noiseless vowel neurogram was smaller than the distances to all the other noiseless neurograms. In the case where the distance from a noisy neurogram to a noiseless neurogram is greater than the distance from a randomly generated neurogram, it is marked as non-classified.

Figure 6:
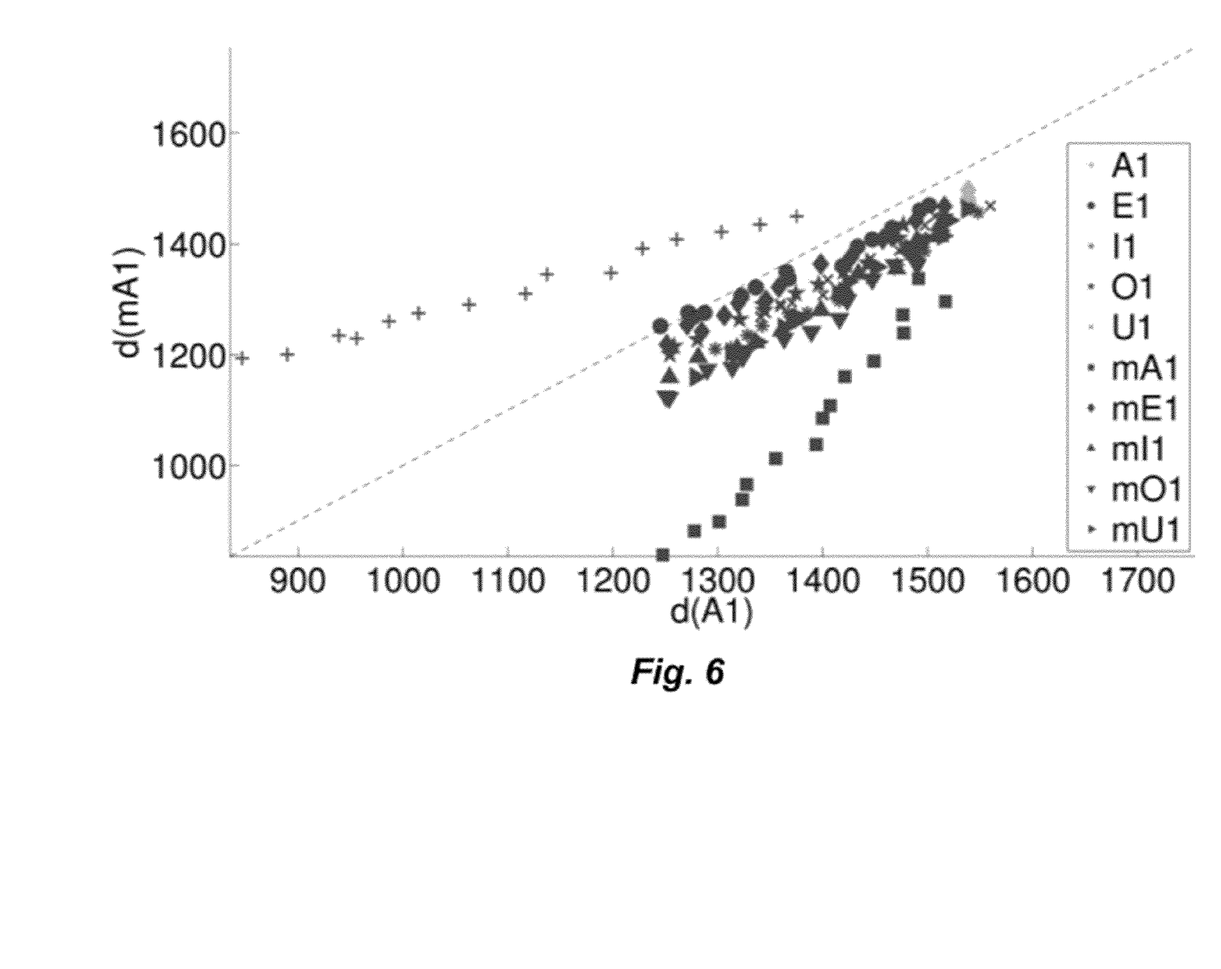
FIG. 6 shows data from a 12 dimensional projection of neurogram data in one set of experiments.

In FIG. 6, each neurogram was assigned a vector of 12 distances to the 12 noiseless neurograms. That 12-dimensional vector can be projected onto any plane spanned by two axes and the discrimination behavior can be observed between the two speech samples belonging to the two axes. The figure shows the correctly classified neurograms versus the non-classified and the incorrectly classified neurograms for different speakers and different noise levels. The figure considers a male and female speakers' utterance of the vowel A and plots the distance between the correct neurogram with the neurogram corresponding to the sound corrupted by pink noise. For the male and female A's, distance increases as noise increases. As the noise increases, the distance between the corresponding neurogram and the non-corrupted neurogram increases but this does not affect the correct classification of the neurogram for very large values of the noise variance.

A general tool for sound quality evaluation is PEAQ (Perceptual Evaluation of Audio Quality)(C. Colomes, C. Schmidmer, T. Thiede, W. C. Treurniet, "Perceptual Quality Assessment for Digital Audio: PEAQ—The new ITU standard for objective Measurement of perceived audio quality", Audio Engineering Society Conference: 17th International Conference: High Quality Audio Coding, 1999; incorporated herein by reference in its entirety) from OPTICOM GmbH which is an algorithm to evaluate audio quality on a perceptual basis. PEAQ compares the (degraded) output of a given device with the input signal as reference and estimates the perceived audio quality based on psychoacoustic parameters. Embodiments of the present invention inherently consider the different psychoacoustic parameters as they are part or consequence of the auditory model which is used. Therefore the described techniques for neurogram comparison also are able to measure the sound degradation arising from lossy compression techniques or other sound processing devices.

Figure 7:
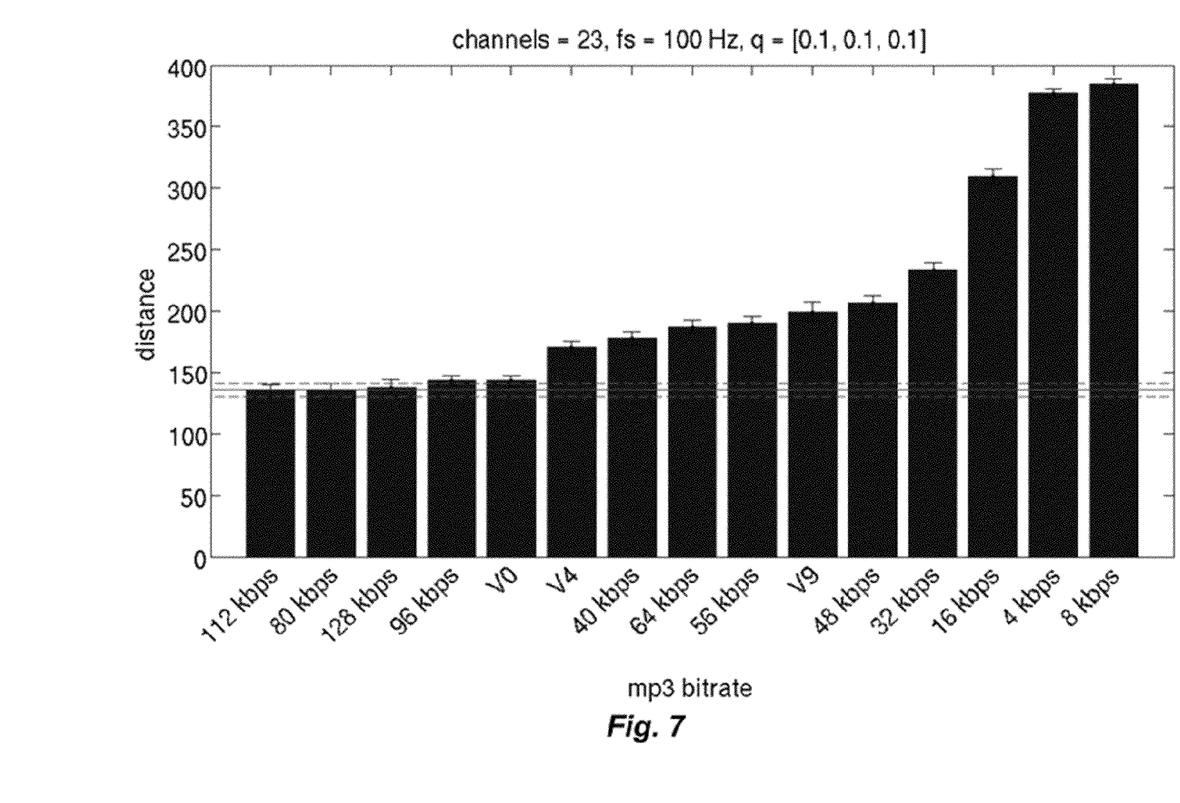
FIG. 7 shows data from mp3 bitrate experiments with neurogram evaluation.

In one set of experiments, neurograms were produced of mp3-compressed speech samples using the LAME-Encoder. Different mp3 bitrates presented to the auditory model from Wang ("Speech coding and information processing in the peripheral human auditory system", Dissertation, TUM, 2010; incorporated herein by reference) and the obtained neurograms were set in reference to a neurogram which was generated by the original (uncompressed) source sound file. The resulting distance between the neurograms can be used as a measure of degradation by sound compression. FIG. 7 shows a ranking of all the neurograms generated with different bitrates where the thin line parallel to the horizontal axis indicates the level of self-similarity of the uncompressed neurograms. Error bars indicate variance under multiple representations to the auditory model. V0, V4 and V9 are high, medium and low quality encoded mp3 s with variable bitrate. There is a clear tendency that greater compression results in higher distance from the uncompressed case. The proposed tool does not correctly rank the best performing sound compression, but this is coherent with perceptual sensibilities (high fidelity compression degrades perception very little) and well within the error margins. The neurograms used in this numerical example were downsampled to 23 frequency channels and 100 Hz sampling frequency in time and already in this actually very coarse representation of the neuronal sound information there are detectable quality differences between bitrates.

One application of embodiments of the present invention is to evaluate cochlear implant coding strategies. The proposed distance can be used as a metric to compare the electrically evoked activation of the auditory nerve with the case of the normal hearing inner ear. That is models of both intact inner ears and the deaf ear with a cochlear implant can be evaluated based on a quantitative measure which indicates how much the electrically evoked neural activity deviates from the auditory nerve response of the intact inner ear. This can be done with different temporal resolutions, for example, for the rate-place code only (temporal resolution>10 msec) and/or for the evaluation of the coding of the temporal fine-structure (resolution<1 msec).

More generally, embodiments can be applied to compare how close different cochlear implant coding strategies reach a target function. Specific hearing impairments can be modeled by changing the parameters of the local and the global similarity to match the specific hearing performance. The response pattern of a healthy inner ear would be a measure for the naturalness of the coding, but the specific target can be any beneficial function depending on the circumstances and appropriate costs can be selected for transformations, for example, there can be shifts of the spectro-temporal response patterns along the frequency-place axes without cost assuming that the brain will compensate a shift of the place map.

A metric as above that describes the distance of a response to a target response enables optimization of a CI coding strategy (or a complete CI system). This provides a powerful way to develop new CI coding strategies because it replaces the commonly used trial-and-error evaluation which relies on educated guesses with a much more systematic approach.

During the optimization, the electrical stimulation patterns for every time-step are changed until the distance of the elicited response to the target response reaches a minimum. After this first adaptation step has been performed the optimal stimulation values for every time step is determined. However, these stimulation values only hold for the sound signal they are optimized for. For a CI coding strategy the stimulation rules need to be derived by comparing this optimal response to the properties of the sound signal. This issue is equivalent to reversing the electrical excitation process which elicits the neuronal response patterns (this is the model for electrical stimulation). The coding strategies can be derived from a model of the intact inner ear and/or from a simpler representation of the input sound such as its spectrogram. Using computational models of the impaired ear with hearing prostheses more generally, the techniques described above can be applied to optimize the processing strategies that are used.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware.

Although various exemplary embodiments of the invention have been disclosed, it should be apparent to those skilled in the art that various changes and modifications can be made which will achieve some of the advantages of the invention without departing from the true scope of the invention.

What is claimed is:

1. A method for evaluating a selected hearing stimulation strategy in a hearing impaired patient, the method comprising:
   accessing a healthy neurogram representation of a normal auditory neural response to a selected sound input by a healthy auditory system;
   accessing an impaired neurogram representation of an impaired auditory neural response to the selected sound input by a hearing impaired patient auditory system using the hearing stimulation strategy; and
   comparing the impaired neurogram to the healthy neurogram based on:
      i. partitioning the neurograms into corresponding temporal and frequency domain tiles,
      ii. determining local variability between corresponding individual tiles by comparison of selected tile features,
      iii. determining global variability between the neurograms by weighted averaging of the comparison of the selected tile features, and
      iv. developing from the local and global variabilities a perception estimate representing effectiveness of the selected hearing stimulation strategy in approaching normal healthy hearing for the implanted patient.

2. A method according to claim 1, wherein the perception estimate further is based on a computational model of a hearing prosthesis using the selected hearing stimulation strategy.

3. A method according to claim 1, wherein the local variability is determined based on a Levenshtein distance or an approximation thereof between the selected tile features.

4. A method according to claim 3, wherein a Needleman-Wunsch algorithm or an approximation thereof is used for evaluating or estimating the Levenshtein distance.

5. A method according to claim 4, wherein the Needleman-Wunsch algorithm is applied to a matrix containing neurogram instantaneous firing rate.

6. A method according to claim 1, wherein a weighted partition sum is used for determining global variability.

7. A method according to claim 1, wherein a rate-place code with temporal resolution greater than 300 milliseconds is used for comparing the neurograms.

8. A method according to claim 1, wherein temporal fine structure with temporal resolution higher than 1 millisecond is used for comparing the neurograms.

9. A non-transitory computer readable storage medium having stored therein a plurality of instructions configured for causing one or more processors to execute the steps of:
  accessing a healthy neurogram representation of a normal auditory neural response to a selected sound input by a healthy auditory system;
  accessing an impaired neurogram representation of an impaired auditory neural response to the selected sound input by a hearing impaired patient auditory system using the hearing stimulation strategy; and
  comparing the impaired neurogram to the healthy neurogram including:
  i. partitioning the neurograms into corresponding temporal and frequency domain tiles,
  ii. determining local variability between corresponding individual tiles by comparison of selected tile features,
  iii. determining global variability between the neurograms by weighted averaging of the comparison of the selected tile features, and
  iv. developing from the local and global variabilities a perception estimate representing effectiveness of the selected hearing stimulation strategy in approaching normal healthy hearing for the implanted patient.

10. A product according to claim 9, wherein the perception estimate further is based on a computational model of a hearing prosthesis using the selected hearing stimulation strategy.

11. A product according to claim 9, wherein the step for determining local variability uses Levenshtein distance or an approximation thereof between the selected tile features.

12. A product according to claim 11, wherein the step for determining local variability uses a Needleman-Wunsch algorithm for evaluating the Levenshtein distance.

13. A product according to claim 12, wherein the step for determining local variability applies the Needleman-Wunsch algorithm or its possible approximations to a matrix containing neurogram instantaneous firing rate.

14. A product according to claim 9, wherein the step for determining global variability uses a weighted partition sum.

15. A product according to claim 9, wherein the step for comparing the neurograms uses a rate-place code with temporal resolution higher than 300 milliseconds.

16. A product according to claim 9, wherein the step for comparing the neurograms uses temporal fine structure with temporal resolution higher than 1 millisecond.

* * * * *